United States Patent
Abuzaina

(10) Patent No.: US 9,107,570 B2
(45) Date of Patent: Aug. 18, 2015

(54) SYSTEM AND METHOD FOR MAPPING ANATOMICAL STRUCTURES AND MARKING THEM ON A SUBSTRATE

(71) Applicant: Covidien LP, Mansfield, MA (US)

(72) Inventor: Ferass Abuzaina, Shelton, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/898,887

(22) Filed: May 21, 2013

(65) Prior Publication Data

US 2013/0338437 A1 Dec. 19, 2013

Related U.S. Application Data

(60) Provisional application No. 61/661,563, filed on Jun. 19, 2012.

(51) Int. Cl.
*A61B 1/04* (2006.01)
*A61B 1/313* (2006.01)
*A61F 2/00* (2006.01)
*A61B 1/00* (2006.01)

(52) U.S. Cl.
CPC ......... *A61B 1/00043* (2013.01); *A61B 1/00009* (2013.01); *A61B 1/04* (2013.01); *A61B 1/3132* (2013.01); *A61F 2/0063* (2013.01); *A61F 2240/002* (2013.01); *A61F 2250/0097* (2013.01)

(58) Field of Classification Search
CPC ...... A61F 2/30942; A61F 2/02; A61F 2/0063
USPC ........ 600/103, 101, 104, 114; 348/45; 396/17
See application file for complete search history.

(56) References Cited

U.S. PATENT DOCUMENTS

| | | | |
|---|---|---|---|
| 4,976,737 A | 12/1990 | Leake | |
| 5,000,172 A | 3/1991 | Ward | |
| 5,749,842 A | 5/1998 | Cheong et al. | |
| 6,235,964 B1 | 5/2001 | Kadash et al. | |
| 6,436,030 B2 | 8/2002 | Rehil | |
| 7,044,982 B2 | 5/2006 | Milbocker | |
| 7,401,413 B1 | 7/2008 | Nelson | |
| 7,850,454 B2 | 12/2010 | Toly | |

(Continued)

FOREIGN PATENT DOCUMENTS

WO 0180788 A2 11/2001

OTHER PUBLICATIONS

Pickhardt et al. (Atlas of Gastrointestinal Imaging: Radiologic-Endoscopic Correlation, 1st Ed., May 9, 2007) 1 Page.*
Bjork, "Why Crop a Photo?", retrieved from the Wayback machine at https://web.archive.org/web/20100130011923/http://www.digicamhelp.com/processing-photos/basic-editing/why-crop-a-photo, Jan. 30, 2010, 5 pages*

(Continued)

*Primary Examiner* — Anhtuan T. Nguyen
*Assistant Examiner* — Timothy J Neal

(57) ABSTRACT

The present disclosure provides a method and system for mapping anatomical structures and marking them on an image to be printed on a substrate including the steps of inserting an imaging device into a surgical site, obtaining an image of a defect located in the surgical site from the imaging device, adjusting the image, transmitting the image to a printer, and printing the image on a substrate. The printed image may be a size directly proportional to the defect. The adjusting step may further include the steps of setting a minimum margin to be maintained between the perimeter of the defect and the perimeter of the substrate, selecting a shape and size of the substrate, and identifying at least one anatomical feature of the surgical site.

7 Claims, 6 Drawing Sheets

(56) References Cited

U.S. PATENT DOCUMENTS

| | | |
|---|---|---|
| 2001/0049539 A1 | 12/2001 | Rehil |
| 2004/0019360 A1 | 1/2004 | Farnsworth et al. |
| 2004/0147839 A1 | 7/2004 | Moctezuma de la Barrera et al. |
| 2004/0242961 A1* | 12/2004 | Bughici et al. ............... 600/108 |
| 2005/0026125 A1* | 2/2005 | Toly ............................. 434/262 |
| 2005/0275137 A1 | 12/2005 | Stolpe et al. |
| 2009/0226068 A1 | 9/2009 | Fitz et al. |
| 2009/0281558 A1 | 11/2009 | Li |
| 2011/0295283 A1 | 12/2011 | Darois et al. |

OTHER PUBLICATIONS

Bjork, "6 Reasons to crop a photo", retrieved at http://www.digicamhelp.com/processing-photos/basic-editing/why-crop-a-photo/, Jan. 21, 2015, 10 pages.*
Adobe Photoshop CS3 User Guide Ps, Copyright 2007, 681 pages.*
European Search Report, Application No. EP 13 17 2560, dated Jan. 29, 2014.
European Search Report, Application No. EP 14 15 6517 dated Apr. 4, 2014.

* cited by examiner

SYSTEM AND METHOD FOR MAPPING ANATOMICAL STRUCTURES AND MARKING THEM ON A SUBSTRATE

CROSS-REFERENCE TO RELATED APPLICATIONS

The present application claims priority to, and the benefit of, U.S. Provisional Patent Application Ser. No. 61/661,563, filed on Jun. 19, 2012, the entire contents of which are incorporated herein by reference.

BACKGROUND

1. Technical Field

The present disclosure relates to an apparatus and method for mapping of internal anatomical features and printing them on a substrate. More particularly, the present disclosure relates to providing an internal probe to capture an image of a surgical site with anatomical features and a printing device for printing the image of the anatomical features on a mesh substrate.

The present application claims priority to, and the benefit of, U.S. Provisional Patent Application Ser. No. 61/661,563, filed on Jun. 19, 2012, the entire contents of which are incorporated herein by reference.

2. Description of the Related Art

Image guided surgery has become more and more common, in part because of the ability of a surgeon to view internal images of a patient's anatomy and pre-plan a medical operation. In this way, for example, pre-acquired images of the anatomical body are used to plan the course of the medical procedure, whether the medical procedure is diagnostic, therapeutic, or surgical in nature. The pre-acquired images may also be used, to some extent, during the medical procedure for orientation of the surgeon with respect to the internal anatomy of the patient.

The images of a patient's external or internal anatomy used in image guided surgery may be generated by, for example, computerized tomography (CT), magnetic resonance imaging (MRI), video, ultrasound, and X-rays. Images may also be captured using angiography, single photon emission computer tomography, and positron emission tomography (PET).

Hernias are abnormal protrusions of an organ or other body structure through a defect or natural opening in a covering membrane, e.g., a wall of a cavity that normally contains the organ or other body structure. For example, inguinal hernias are, typically, caused by soft tissue from the intestines protruding through the inguinal wall. Ventral hernias, on the other hand, are caused by internal organs pushing through to a weak spot in the abdominal wall.

The use of prosthetic mesh has now become accepted practice in the treatment of patients with both inguinal and ventral hernias, as well as other types of hernias, e.g., hiatal, femoral, umbilical, diaphragmatic, etc. To endoscopically apply the mesh for hernia repair, a surgical region (i.e., adjacent the cavity wall) is, typically, insufflated. Subsequently, a surgeon selects points on the cavity wall where the surgeon believes a peripheral edge of the mesh, i.e., the expected corners of a mesh (assuming a rectangular mesh), will be affixed.

In certain instances, prior to affixing the mesh, the mesh is, initially, held in position by pressing on the mesh from outside the body while observing the mesh through a laparoscope or, conversely, pressing upward against the mesh with the use of one or more suitable devices, e.g., an atraumatic grasper or the like. Thereafter, the surgical mesh is often affixed, e.g., sutured or tacked using a fastener, to the cavity wall by conventional techniques.

Unfortunately, this method has shortcomings. Once the mesh is initially held in position, a surgeon does not know what anatomical features are located behind the mesh. When suturing or tacking the mesh to the surface, the surgeon must be aware of the anatomical features behind the mesh so as to avoid tacking or stapling into nerves or blood vessels, which can cause acute and chronic pain as well as bleeding. Accordingly, a need exists for mapping the anatomical structures and marking them on the mesh so the surgeon will be aware of the proper suturing positions when affixing the mesh to the tissue surface.

SUMMARY

The present disclosure provides a method for mapping anatomical structures and marking them on an image to be printed on a substrate. The method includes the steps of inserting an imaging device into a surgical site, obtaining an image of a defect in the surgical site from the imaging device, adjusting the image, transmitting the image to a printer, and printing the image on a substrate. The printed image may be a size directly proportional to the defect in the surgical site. The adjusting step may further include the steps of setting a minimum margin to be maintained between the perimeter of the defect and the perimeter of the substrate, and measuring the defect. Additionally or alternatively, the adjusting step may further include identifying at least one anatomical feature of the surgical site and marking the anatomical feature on the image. Additionally or alternatively, a substrate of sufficient size and/or shape may be selected which maintains the minimum margin between the perimeter of the defect and the perimeter of the substrate. Additionally, the image may be previewed and edited prior to being printed on the substrate. The method may further include the steps of inserting the substrate into the surgical site and aligning the substrate over the defect in the surgical site. Additionally, the method may further include the steps of obtaining a second image of the defect in the surgical site with the substrate over the defect and comparing the first image to the second image.

In some embodiments, the substrate that the image is printed on is a mesh. Alternatively, the substrate that the image is printed on is a starch based paper, e.g., rice paper, where the starch based paper is attached to a mesh.

The present disclosure also provides a system for mapping anatomical structures and marking them on an image to be printed on a substrate including an image capturing unit for capturing an image of a defect in a surgical site, an image processing unit for adjusting the captured image, and a transmitting unit for transmitting the image to a printer for printing the image on a substrate. The printed image may be a size directly proportional to defect in the surgical site. The image processing unit may further be configured to set a minimum margin to be maintained between the perimeter of the defect and the perimeter of the substrate, measure the size of the defect, and select a shape and size of the substrate sufficient to maintain the minimum margin set. Additionally or alternatively, the image processing unit may identify at least one anatomical feature of the surgical site and mark the anatomical features on the image to be printed on the substrate. Additionally, the image processing unit may preview and edit the image for printing.

In some embodiments of the system, the substrate that the image is printed on is a mesh. Alternatively, the substrate that the image is printed on is a starch based paper, e.g., a rice paper, where the starch based paper is attached to a mesh.

BRIEF DESCRIPTION OF THE DRAWINGS

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
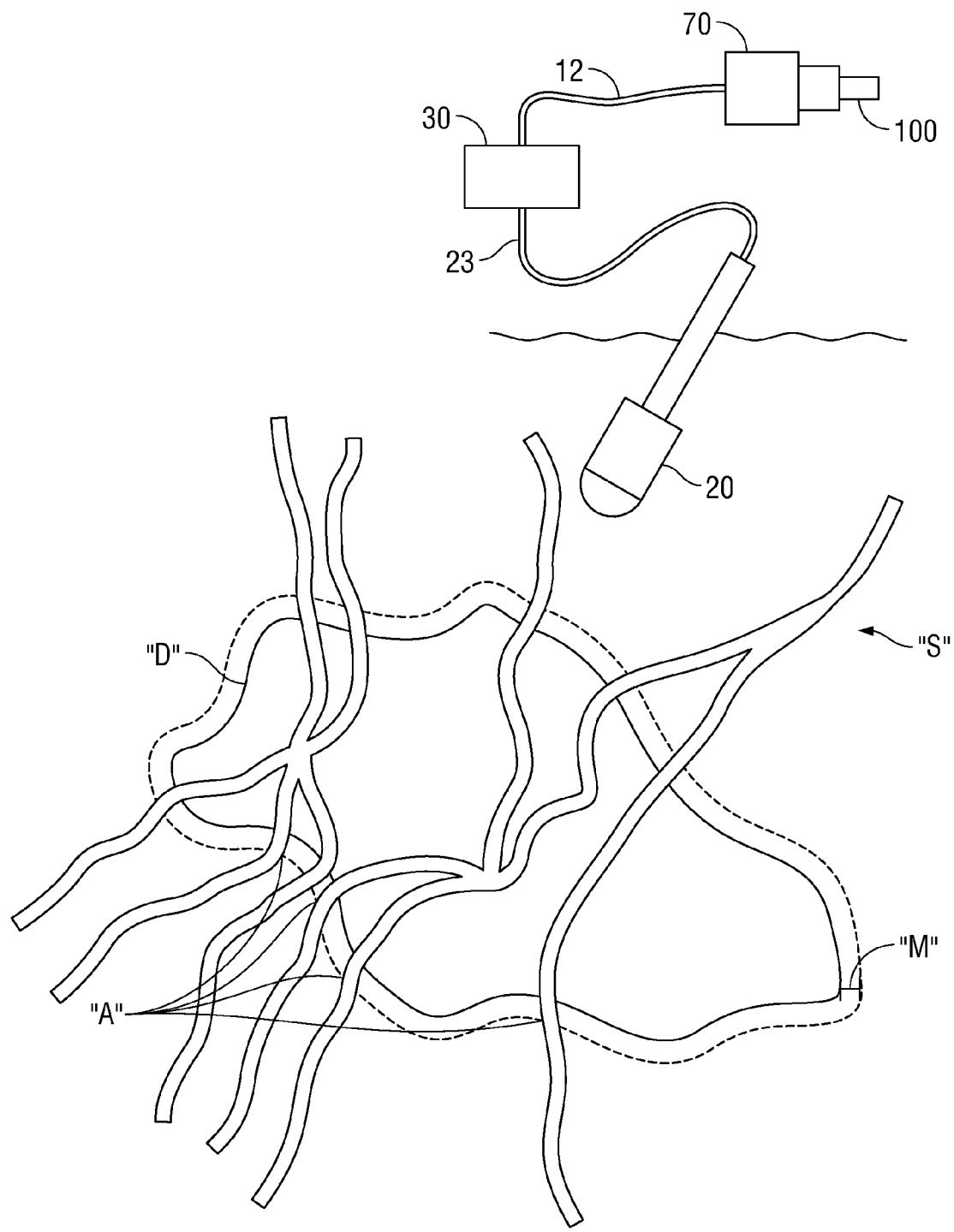
FIG. 1 is a perspective view of a system according to an embodiment of the present disclosure.

Referring to FIG. 1, there is disclosed a system 10 for use in minimally invasive surgery. The system 10 is configured to map anatomical structures or features "A" of a surgical site "S" and mark the anatomical features "A" on a substrate 100. System 10 includes an image capturing unit 20, an image processing unit 30, and a printing unit 70. Image capturing unit 20 is configured to obtain or capture an image of the surgical site "S." Surgical site "S" includes a defect "D", for example a hernia defect, and anatomical features "A." All or a portion of the anatomical features "A" may be disposed on all or a portion of the defect "D" of the surgical site Continuing with reference to FIG. 1, the image capturing unit 20 is operatively coupled to the image processing unit 30 via line 23. Although image capturing unit 20 is shown as being operatively coupled to image processing unit 30 via line 23, image capturing unit 20 may be coupled to image processing unit 30 by any means, such as, without limitation, wirelessly. Image processing unit 30 is operatively coupled to printing unit 70 via cable 12. Although image processing unit 30 is shown as being operatively coupled to printing unit 70 via cable 12, image processing unit 30 may be coupled to printing unit 70 by any means, such as, without limitation, wirelessly. Additionally, or alternatively, image capturing unit 20 may be operatively coupled to printing unit 70 directly, and image capturing unit 20 may be configured to perform all of the operations of image processing unit 30. Additionally, or alternatively, image capturing unit 20 may be operatively coupled to printing unit 70, and printing unit 70 may be configured to perform all of the operations of image processing unit 30.

The image capturing unit 20 is positioned within a surgical site "S" to obtain an image of the defect "D" and all of the anatomical features "A" and transmit the image to the image processing unit 30. As described above, the image capturing unit 20 may transmit the image to the image processing unit 30 via line 23 or a wireless connection (not shown).

The image processing unit 30 is configured to adjust and/or scale the image captured by the image capturing unit 20. In addition, the image processing unit 30 may be configured to measure the size of the defect "D" and may further be configured to identify a perimeter, i.e., edges, of the defect "D." Additionally, or alternatively, a user may manually measure the size of the defect "D" and input the measurements via a graphic user interface.

Upon adjusting and/or scaling the image, the image processing unit 30 may further be configured to set a desired minimum margin "M" based on the edges of a portion of the surgical site "S" and the edges of defect "D." The minimum margin "M" may be automatically set by the image processing unit 30 or it may be selected by the user, as will be described in further detail below. The minimum margin "M" acts as a reference point to indicate the minimum distance required between the perimeter, i.e., edges, of the defect "D" and the edge of the substrate 100. By setting a minimum margin "M," an appropriate shape and/or size substrate 100 may be selected, as will be described in further detail below. The minimum margin "M" acts as only a minimum value, and it is understood that the edge of the substrate 100 may exceed the minimum value as allowed by the surgical site "S" and/or as desired by the user. Additionally, or alternatively, and as will be described in further detail below, the portion or area defined by the minimum margin "M" may be a region where a user/surgeon may affix the substrate 100 to the surgical site "S" over the defect "D."

Upon setting a desired minimum margin "M," the image processing unit 30 may further be configured to select an appropriate substrate 100 shape and/or size from a collection of common shapes and sizes based on the measured size of the defect "D," the minimum margin "M" required between the edge of the defect "D" and the edge of the substrate 100, and the surgical site "S." It is preferred that the size of the substrate 100 is large enough to overlap each minimum margin "M," without exceeding the size of the surgical site "S." However, the size of the substrate 100 may be the same size of the region defined by the defect and the combined minimum margins "M." Additionally, or alternatively, a user may select a substrate 100 shape and the image processing unit 30 would then select the appropriate size of the selected shape in accordance with the set minimum margins "M" so that the substrate 100 will be sure to properly fit over the defect "D."

As described above, the image processing unit 30 may be further configured to identify the edges of the defect "D" and mark the edges of the defect "D" on the image. The identification and marking of the edges of the defect "D" may be accomplished by means of image recognition software. Additionally or alternatively, image processing unit 30 may be operated by a user via a graphical user interface and a surgeon/user may identify and/or mark the edges of the defect "D" manually via a graphical user interface.

In addition, the image processing unit 30 may be configured to identify and mark the anatomical structures or features "A," such as, without limitation, arteries, bones, and the like on the image for printing on the substrate 100. The identification and marking of the anatomical structures or features "A" on the image may be accomplished by means of image recognition software. Additionally or alternatively, as noted above, the image processing unit 30 may be operated by a user via a graphical user interface and a surgeon/user may identify and/or mark the anatomical structures or features "A" on the image manually via the graphical user interface.

In addition, the image processing unit 30 may be further configured to optimize the substrate 100 placement to achieve the desired minimum margins "M" around the perimeter of the defect "D." More particularly, subsequent to substrate 100 placement on the defect "D," if the substrate 100 does not line up with the margins "M," the image processing unit 30 is configured to re-select a second substrate 100 shape and/or size that would be sufficient to maintain the minimum margin "M" around the entire perimeter of defect "D."

Image processing unit 30 transmits the adjusted image to the printing unit 70 for printing the image onto a substrate 100. Image processing unit 30 may be connected to printing unit 70 wirelessly (not shown) or via wire 12 as shown.

Continuing with reference to FIG. 1, printing unit 70 is configured to print the image captured by image capturing unit 20 subsequent to proper adjustment by image processing unit 30. Printing unit 70 prints the image on a substrate 100 which can take the form of a mesh 100*a* (FIG. 2A) or a film 100*b* (FIG. 2B) which can be attached to a mesh 100*c* (FIG. 2B). The printing unit 70 prints the image captured including all of the anatomical features "A" which were identified and marked by the image processing unit 30 onto film 100*b* (FIG. 2B). Subsequent to printing the image onto the film 100*b*, film 100*b* may be attached to a mesh 100*c* (FIG. 2B). Alternatively, the printing unit 70 prints the image captured by the image capturing unit 20 including all of the anatomical features "A" which were identified and marked by the image processing unit 30 directly onto the mesh 100*a* (FIG. 2A).

Figure 2A:
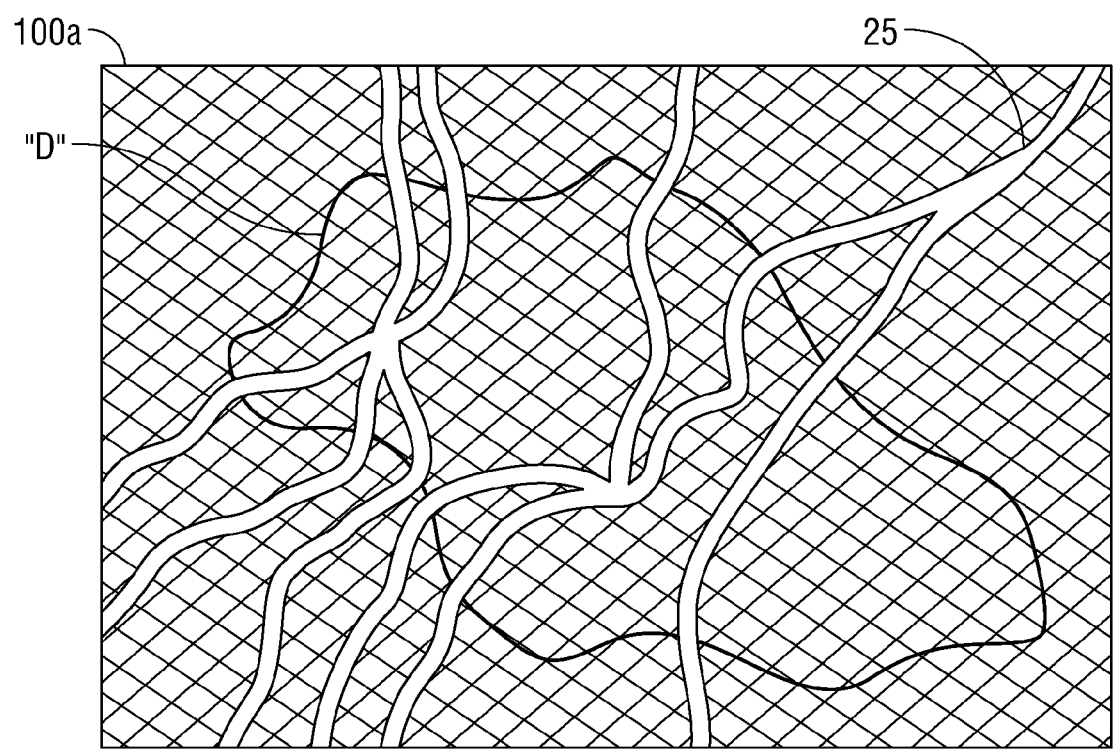
FIG. 2A is a perspective view of a mesh according to an embodiment of the present disclosure.
Figure 2B:
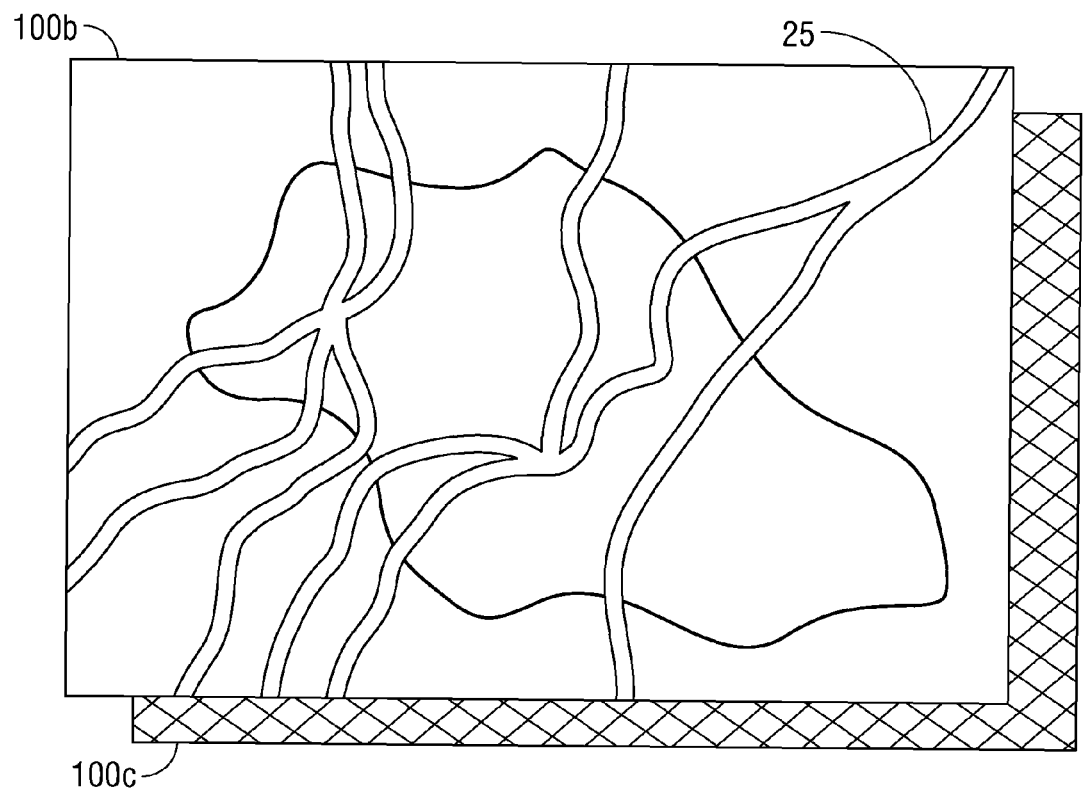
FIG. 2B is a perspective view of a film before being attached to a mesh substrate according to an embodiment of the present disclosure.

Turning now to FIG. 2A, the substrate 100 is shown as a mesh 100*a*. The surgical mesh 100*a* and 100*c* (FIG. 2B) described herein may include porous fabrics made from intertwined filaments. The filaments may be monofilaments or multi-filaments and, in embodiments, a plurality of multi-filaments may be combined to form yarns. The filaments may extend horizontally and vertically in a manner which produces sections where the filaments cross-over one another creating points of common intersection. The surgical mesh 100*a* and/or 100*c* (FIG. 2B) may be woven, non-woven, knitted or braided. In some embodiments, the filaments may form two-dimensional or three-dimensional meshes.

Figure 3:
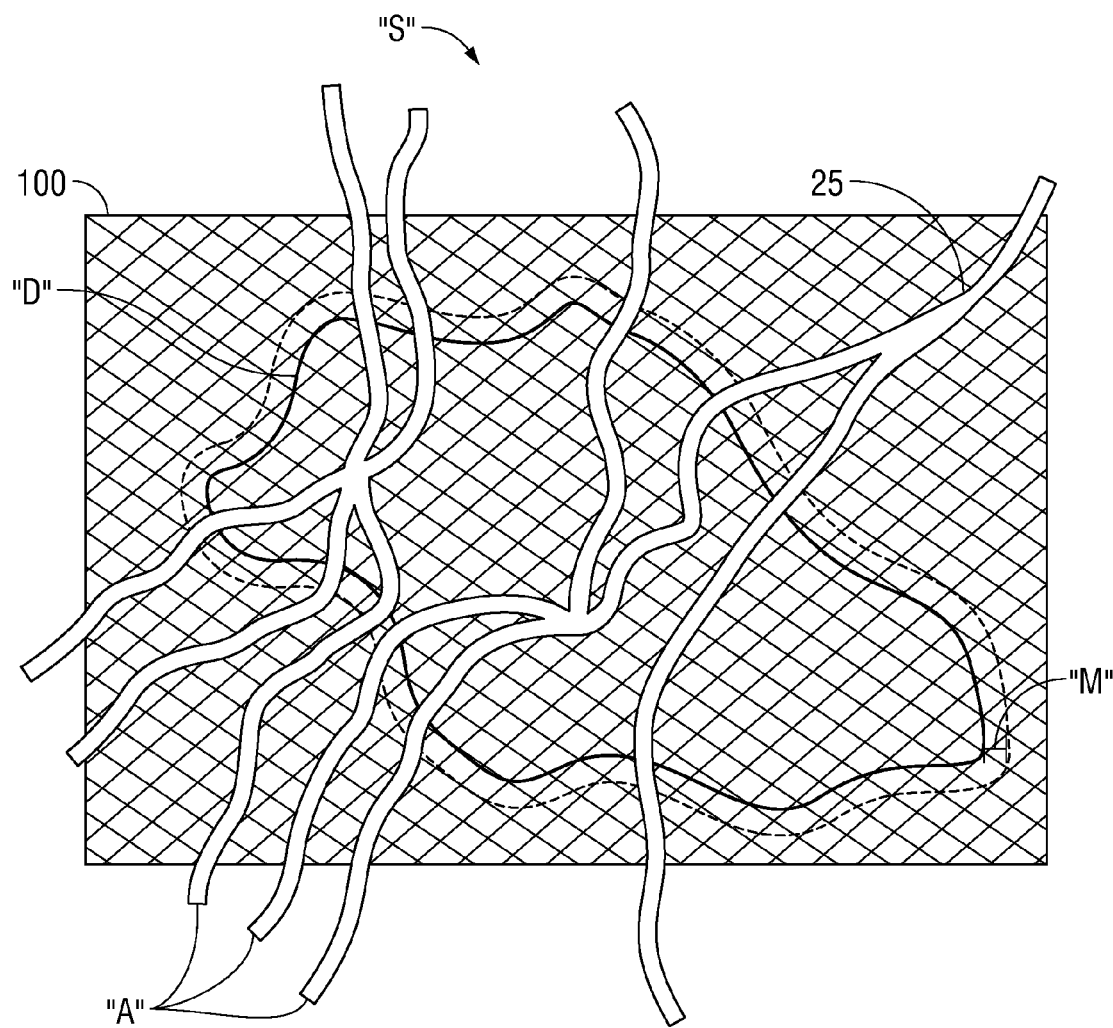
FIG. 3 is a view of the printed image on the mesh placed over a hernia according to an embodiment of the present disclosure.

Continuing with reference to FIG. 2A, the image is printed directly on to the mesh 100*a* which includes landmarks 25. Landmarks 25 are printed images of the anatomical features "A" (FIGS. 1 and 3) which would be present behind the mesh 100*a* when the mesh 100*a* is placed over the defect "D" in the surgical site "S" (FIGS. 1 and 3). Landmarks 25 assist a surgeon in providing the surgeon with an image of the anatomical features "A" which are located behind the mesh 100*a*. With landmarks 25 in sight, a surgeon may avoid tacking, or otherwise affixing, those areas in which anatomical features "A" are located by not tacking, or otherwise affixing, in regions where the landmarks 25 are visible. Additionally, or alternatively, landmarks 25 may assist a surgeon with proper placement of mesh 100*a* over the defect "D" of the surgical site "S." Specifically, a surgeon may line up each edge of the landmarks 25 with the corresponding anatomical feature "A" so as to ensure proper placement of the mesh 100*a*.

Although mesh 100*a* is shown as a rectangular shape in FIG. 2A, it is understood that mesh 100*a* will take the shape/size as set by image processing unit 30 (FIG. 1) or as set by the user, as described above. It is understood that any given distance between the edge of mesh 100*a* and the edge of defect "D" may not be lower than the distance set as the minimum margin "M" (FIG. 1).

Turning now to FIG. 2B, substrate 100 is shown as a film 100*b* which is configured to attach to a mesh 100*c*, similar to the mesh of 100*a* described above. The image captured by image capturing unit 20 and adjusted by image processing unit 30 may be printed by printing unit 70 directly onto film 100*b*. The film 100*b* may be a biopolymer or film such as, without limitation, a starch-based paper such as rice-film. As shown in FIG. 2B, landmarks 25 are printed directly onto the film 100*b* which represent the anatomical features "A" on the defect "D" of the surgical site "S." Subsequent to printing the image onto the film 100*b*, the film 100*b* is adhered to the mesh 100*c*. As described above with respect to mesh 100*a*, with landmarks 25 of mesh 100*c* in sight, a surgeon may avoid tacking, or otherwise affixing, those areas in which anatomical features "A" are located by not tacking, or otherwise affixing, in regions where the landmarks 25 are visible. Additionally, or alternatively, landmarks 25 may assist a surgeon with proper placement of mesh 100*c* over the defect "D" of the surgical site "S." Specifically, a surgeon may line up each edge of the landmarks 25 with the corresponding anatomical feature "A" so as to ensure proper placement of the mesh 100*c*.

Although film 100*b* and mesh 100*c* are shown as a rectangular shape in FIG. 2B, it is understood that film 100*b* and mesh 100*c* may take the shape/size as set by image processing unit 30 (FIG. 1) or as set by the user, as described above. It is understood that any given distance between the edge of film 100*b* and mesh 100*c* and the edge of defect "D" may not be lower than the distance set as the minimum margin "M" (FIG. 1).

Turning now to FIG. 3, substrate 100, i.e., mesh 100*a*, or film 100*b* and mesh 100*c*, is shown placed over the defect "D" of the surgical site "S." All or a portion of anatomical features "A" are covered by substrate 100. Substrate 100 includes landmarks 25 in the portions where anatomical features "A" are blocked by substrate 100. Landmarks 25 may be used by a surgeon to identify which portions of the substrate 100 may not be tacked, or otherwise affixed, thereby assisting the surgeon in identifying regions that should not be tacked, or otherwise affixed, i.e., regions including anatomical features "A."

Figure 4:
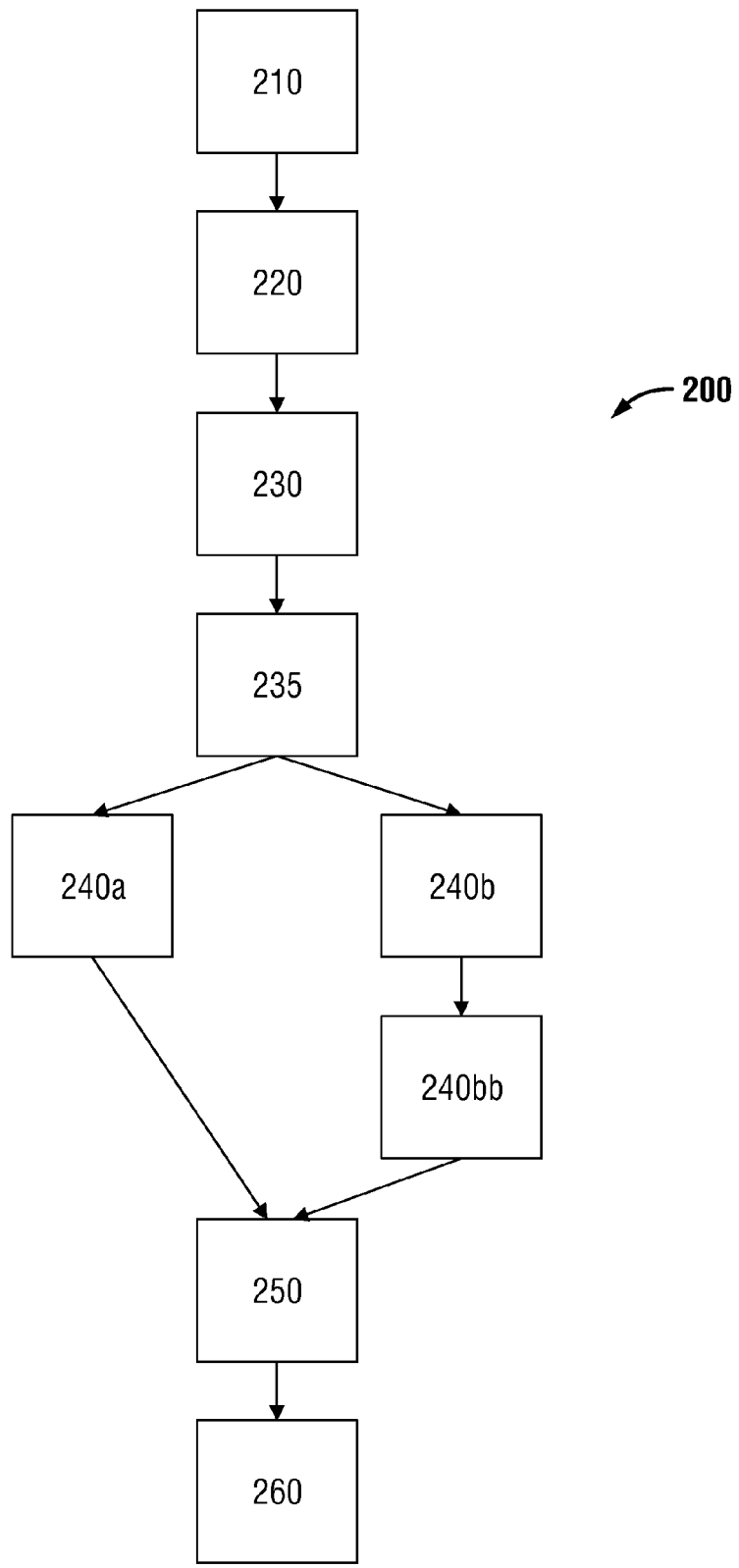
FIG. 4 is a flow-chart of a method for mapping anatomical structures according to an embodiment of the present disclosure.

Turning now to FIG. 4, a method 200 for mapping anatomical features "A" (FIG. 1) on a substrate 100 (FIG. 1) is shown. At step 210, an image capturing unit 20, such as, without limitation, a laparoscope, is inserted into a surgical site "S," i.e., a patient's body through an opening into a cavity. Subsequent to inserting the imaging device 20 into the surgical site "S," at step 220, an image is captured of the surgical site "S" which includes the defect "D" and anatomical features "A."

At step 230, the image processing unit 30 (FIG. 1) adjusts the scale of the image to a desired size and measures the defect "D." Additionally or alternatively, and as described above, the measurement of defect "D" may be carried out manually by the surgeon by means known in the art such as with a tape measure. The manually measured size of defect "D" may then be entered as data into the graphical user interface as described above. As noted above, the image processing unit 30 is configured to adjust and/or scale the image captured by the image capturing unit 20, for example to correct the angle, planarity or size of the image. The image processing unit 30 may further be configured to set a desired minimum margin "M" based on the edges of a portion of the surgical site "S," and the edges of the defect "D." Upon adjusting and/or scaling the image and setting the desired minimum margins "M" to be maintained, the image processing unit 30 may further be configured to select an appropriate substrate 100 shape and/or size from a collection of common shapes and sizes sufficient to maintain the minimum margin "M" and cover the area of defect "D."

At step 235, a determination is made as to whether the image will be printed directly onto mesh 100a (FIG. 2A) or onto film 100b (FIG. 2B). If at step 235 a determination is made to print onto mesh 100a (FIG. 2A) then the method 200 proceeds to step 240a. Alternatively, if at step 235 a determination is made to print onto film 100b (FIG. 2B), the method 200 will proceed to step 240b. The determination may be made by any component of system 10 (FIG. 1) such as, without limitation, image processing unit 30 (FIG. 1). Alternatively, a user may make the determination via the graphical user interface described above.

At step 240a, the printing unit 70 prints the image directly onto the mesh 100a (FIG. 2A). Alternatively, at step 240b, the printing unit 70 prints the image onto a film 100b (FIG. 2B) which is subsequently attached to a mesh 100c (FIG. 2B) at step 240bb.

Continuing with reference to FIG. 4, at step 250, either mesh 100a (FIG. 2A) or mesh 100c (FIG. 2B) with the image of the anatomical features "A" is inserted into the surgical site "S." At step 260, the mesh 100a or 100c is aligned onto the defect "D" such that landmarks 25 (FIG. 3) line up with the anatomical features "A" of the surgical site "S" located around or on the defect "D."

Figure 5:
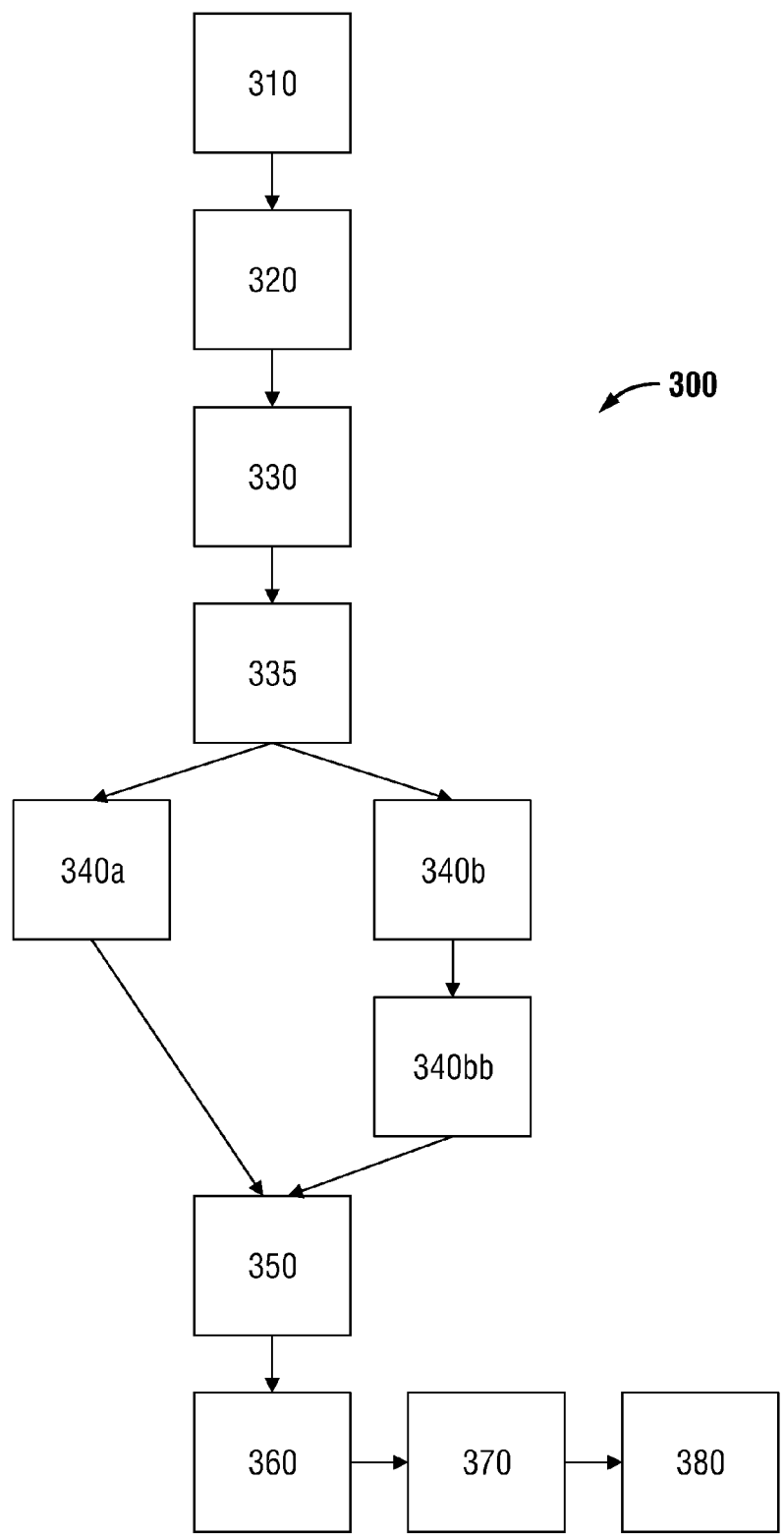
FIG. 5 is a flow-chart of a method for mapping anatomical structures according to a second embodiment of the present disclosure.

Turning now to FIG. 5, a method 300 for mapping anatomical features "A" (FIG. 1) on a substrate 100 (FIG. 1) is shown. At step 310, an image capturing unit 20, such as, without limitation, a laparoscope, is inserted into a surgical site "S," i.e., a patient's body through an opening into a cavity. Subsequent to inserting the imaging device 20 into the surgical site "S," at step 320, a first image is captured of the surgical site "S."

At step 330, the image processing unit 30 (FIG. 1) adjusts the scale of the image to a desired size and measures the defect "D." Additionally or alternatively, and as described above, the measurement of defect "D" may be carried out manually by the surgeon by means known in the art such as with a tape measure. The manually measured size of defect "D" may then be entered as data into the graphical user interface as described above. As noted above, the image processing unit 30 is configured to adjust and/or scale the image captured by the image capturing unit 20. Upon adjusting and/or scaling the image, the image processing unit 30 may further be configured to select an appropriate substrate 100 shape and/or size from a collection of available shapes and sizes. The image processing unit 30 may further be configured to set a desired minimum margin "M" based on the edges of at least a portion of the surgical site "S" and the edges of the defect "D" to ensure that the substrate 100 will be a proper shape and/or size sufficient to maintain the desired minimum margins "M" around the perimeter of defect "D" while covering the area of defect "D." For example, a user could input the desired minimum margin "M" size, e.g., 4 or 5 cm, and the image processing unit 30 could optimize mapping of the defect "D" onto the mesh 100a or the film 100b to ensure that the desired minimum margin "M" is maintained on at least a portion of the substrate 100, including restricting the user's choice of substrate shapes or sizes to only those shapes and sizes sufficient to maintain the desired minimum margin "M" around the perimeter of the defect "D."

At step 335, a determination is made as to whether the image will be printed directly onto mesh 100a (FIG. 2A) or onto film 100b (FIG. 2B). If at step 335 a determination is made to print onto mesh 100a (FIG. 2A) then the method 300 proceeds to step 340a. Alternatively, if at step 335 a determination is made to print onto film 100b (FIG. 2B), the method 300 will proceed to step 340b. The determination may be made by any component of system 10 (FIG. 1) such as, without limitation, image processing unit 30 (FIG. 1). Alternatively, a user may make the determination via the graphical user interface described above.

At step 340a, the printing unit 70 prints the image directly onto the mesh 100a (FIG. 2A). Alternatively, at step 340b, the printing unit 70 prints the image onto a film 100b (FIG. 2B) which is subsequently attached to a mesh 100c (FIG. 2B) at step 340bb.

Continuing with reference to FIG. 5, at step 350, either mesh 100a (FIG. 2A) or mesh 100c (FIG. 2B) with the image of the anatomical features "A" is inserted into the surgical site "S." At step 360, the mesh 100a or 100c is aligned onto the defect "D" such that landmarks 25 (FIG. 3) line up with the anatomical features "A" of the surgical site "S." At step 370 a second image of the surgical site "S" is obtained with the mesh 100a or 100c attached to the defect "D" prior to affixing, i.e., tacking, the mesh 100a or 100c to the defect "D." At step 380, the first image captured at step 320 is compared to the second image captured at step 370 to ensure that the landmarks 25 are aligned with the anatomical features "A" of the surgical site "S" behind the mesh 100a (FIG. 2A) or 100c (FIG. 2B).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for mapping anatomical structures and marking them on a substrate for a surgical procedure, comprising:
    inserting an imaging device into a surgical site;
    obtaining an image of a defect located in the surgical site from the imaging device;
    identifying at least one anatomical feature of the surgical site and marking the at least one anatomical feature on the image;
    setting a minimum margin to be maintained between an edge of the defect and an edge of the substrate;
    measuring the defect;
    transmitting the image to a printer;
    printing the image on the substrate;
    inserting the substrate into the surgical site, wherein the substrate includes the image and the at least one anatomical feature is printed on the substrate as a corresponding landmark; and
    positioning the substrate over the defect such that the corresponding landmark aligns with the at least one anatomical feature.

2. The method of claim 1, wherein the printed image is a size directly proportional to the defect.

3. The method of claim 1, further comprising previewing and editing the image prior to printing the image on the substrate.

4. The method of claim 1, wherein the substrate is a mesh.

5. The method of claim 1, wherein the substrate is a film.

6. The method of claim 5, further comprising attaching the film to a mesh.

7. The method of claim 1, further comprising:
    obtaining a second image of the defect in the surgical site with the substrate aligned over the defect; and
    comparing the first image to the second image.

* * * * *